United States Patent [19]

Cauwenbergh

[11] Patent Number: 5,849,279
[45] Date of Patent: Dec. 15, 1998

[54] AGENT FOR REGULATING THE GREASINESS OF THE SKIN

[75] Inventor: Gerard Frans Maria Jan Cauwenbergh, Vorselaar, Belgium

[73] Assignee: Janssen Pharmaceutica, NV, Beerse, Belgium

[21] Appl. No.: 815,072

[22] Filed: Mar. 11, 1997

Related U.S. Application Data

[62] Division of Ser. No. 540,335, Oct. 6, 1995, Pat. No. 5,641,494, which is a continuation of Ser. No. 302,675, filed as PCT/EP93/00599 Mar. 12, 1993, abandoned.

[30] Foreign Application Priority Data

Mar. 20, 1992 [EP] European Pat. Off. ......... 92.200.797.6

[51] Int. Cl.$^6$ ............................... A61K 7/00; A61K 7/48
[52] U.S. Cl. ..................... 424/70.8; 424/489; 514/848
[58] Field of Search .................. 424/401, 70.8, 424/489; 514/848

[56] References Cited

U.S. PATENT DOCUMENTS

| | | | |
|---|---|---|---|
| 3,575,999 | 4/1971 | Godefroi | 260/309 |
| 4,335,125 | 6/1982 | Heeres | 424/250 |
| 4,772,627 | 9/1988 | Matsui | 514/462 |
| 4,826,689 | 5/1989 | Violanto | 424/489 |
| 4,966,773 | 10/1990 | Gressel | 424/489 |

FOREIGN PATENT DOCUMENTS

| | | |
|---|---|---|
| 178443 | 4/1986 | European Pat. Off. . |
| 0 490 583 A1 | 6/1992 | European Pat. Off. . |
| WO91/02515 | 3/1991 | WIPO . |

*Primary Examiner*—Sally Gardner-Lane
*Attorney, Agent, or Firm*—Mary A. Appollina

[57] ABSTRACT

The use of a compound having the formula

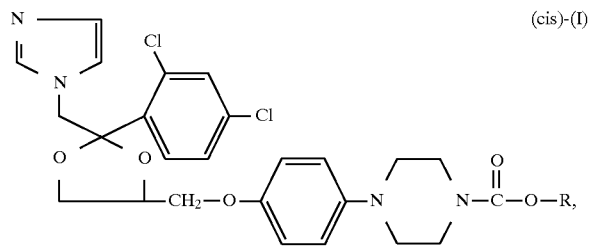

(cis)-(I)

wherein R represents methyl or ethyl, for regulating the greasiness of the skin, particular novel physical forms of said compound, cosmetic compositions comprising said agent, processes for preparing said agent and compositions, and a method of reducing the greasiness of the skin.

4 Claims, No Drawings

AGENT FOR REGULATING THE GREASINESS OF THE SKIN

CROSS-REFERENCE TO RELATED APPLICATIONS

This application is a divisional of application Ser. No. 08/540,335, filed on Oct. 6, 1995, now U.S. Pat. No. 5,641,994, which was a continuation of application Ser. No. 08/302,675, now abandoned, filed on Sep. 9, 1994, which was the national stage of PCT Application Serial No. PCT/EP 93/00599, filed Mar. 12, 1993, which claims priority from European patent application Serial No. 92.200.797.6, filed on Mar. 20, 1992.

A valued aspect of man is the appearance of his skin. A greasy skin, e.g. after a busy day or following physical exercise, is often considered an annoyance, even though it is temporary and does not indicate any health problem. The present invention concerns the use of an agent for regulating the greasiness of the skin, particular novel physical forms of said agent, cosmetic compositions comprising said agent, processes for preparing said agent and compositions, and a method of regulating the greasiness of the skin.

The present invention is concerned with the use of a compound having the formula

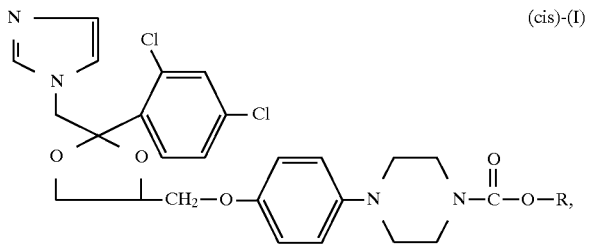

wherein R represents methyl or ethyl, preferably ethyl, or a cosmetically acceptable acid addition salt thereof, for regulating the greasiness of the skin of human beings.

The present invention is also concerned with a method of regulating the greasiness of the skin of human beings, which comprises administering topically to the skin of said human beings a compound having the formula (cis)-(I), or a cosmetically acceptable acid addition salt thereof, in an amount effective in regulating the greasiness of the skin.

The compound (I) can be applied to the skin when necessary or convenient, e.g. at each washing occasion or thereafter. The topical administration may be repeated until a cosmetically beneficial reduction of the greasiness of the skin is obtained. No special precautions are needed other than those which normally apply when using cosmetic agents.

The compounds of formula (I), (±)-methyl- or ethyl-cis-4-[4-[[2-(2,4-dichlorophenyl)-2-(1H-imidazol-1-ylmethyl)-1,3-dioxolan-4-yl]methoxy]phenyl]-1-piperazinecarboxylate used in the method of the present invention are known agents and their preparation as well as their properties are described in U.S. Pat. No. 4,335,125.

The compound of formula (I) is preferably used as such or in a cosmetically acceptable acid addition salt form. Said salt forms can conveniently be prepared by treating the base form with an appropriate acid such as, for example, hydrohalic acids, e.g. hydrochloric or hydrobromic acid, sulfuric acid; nitric acid; phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The term acid addition salt form as used hereinabove also comprises the solvates which the compound compound (I) and its acid addition salts are able to form. Examples of such solvates are, e.g. the hydrates, alcoholates and the like.

The compound (I) is keratinophilic and binds to the keratin in the upper layers of the epidermis. When used in cosmetic compositions at concentrations of 0.05% to 1% (by weight based on the total weight of said cosmetic compositions), in particular 0.1% to 0.5% and preferably 0.1% to 0.2%, compound (I) exerts an inhibitory effect on the formation of sterols such as cholesterol in the skin. Since this influences the lipid contents of the epidermis, a beneficial alteration of the greasiness of the skin results from administering compound (I) to the skin. In particular it appears that the biosynthesis of some free fatty acids is reduced and that the composition of said free fatty acids is altered. Compound (I) also affects the concentration of the phospholipids in the skin. Besides affecting the lipid contents, the compound of formula (I) at the concentrations used also exerts some inhibitory effects on the growth of microorganisms such as bacteria and fungi. Since said microorganisms depend on lipids occuring in the skin, the dual action of compound (I) on both the lipid contents of the skin and on the growth of microorganisms ensures that the skin flora is checked and no unpleasant smells develop.

The compound (I) can be prepared as described in U.S. Pat. No. 4,335,125 or preferably can be obtained from cis-1-acetyl-4-[4-[[2-(2,4-dichlorophenyl)-2-(1H-imidazol-1-ylmethyl)-1,3-dioxolan-4-yl]methoxy]phenyl]piperazine (II) which is a commercial agent. In particular, compound (I) can be prepared by hydrolyzing cis-1-acetyl-4-[4-[[2-(2,4-dichlorophenyl)-2-(1H-imidazol-1-ylmethyl)-1,3-dioxolan-4-yl]methoxy]phenyl]piperazine (II) and reacting the thus obtained product with a reagent of formula W—C(=O)—O—R (III) wherein R represents methyl or ethyl and W represents a leaving group such as halo, preferably chloro, methoxy or ethoxy.

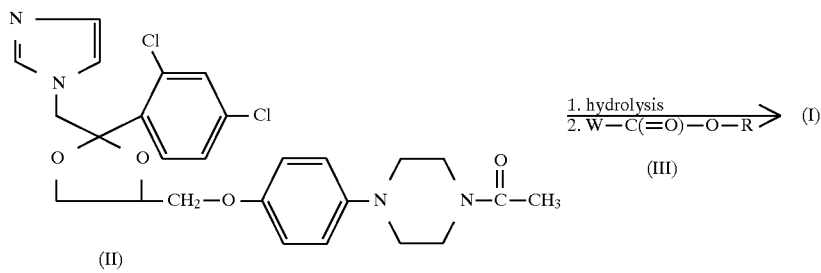

Said hydrolysis can conveniently be conducted by stirring and heating a solution of cis-1-acetyl-4-[4-[[2-(2,4-dichlorophenyl)-2-(1H-imidazol-1-ylmethyl)-1,3-dioxolan4-yl]methoxy]phenyl]piperazine (II) in water in the presence of a base or an acid, preferably in the presence of concentrated hydrochloric acid. The hydrolysis product is extracted from the reaction mixture (neutralized with a base such as sodium or potassium hydroxide) with an organic solvent such as a halogenated hydrocarbon, e.g. dichloromethane, or an alcohol, e.g. methanol, ethanol and the like, or a mixture of such solvents. After evaporation of the organic layer, the crude hydrolysis product need not be purified and can be converted into compound (I) directly by dissolving it into a halogenated hydrocarbon, e.g. dichloromethane and treating it with methyl or ethyl chloroformate in the presence of a base such as sodium or potassium carbonate. Stirring of the reaction mixture enhances the reaction rate and the reaction can conveniently be conducted at room temperature.

In the method according to the present invention it is advantageous to use a micronized form of the compound (I), in particular material having an average particle size of less than 100 microns, preferably less than 75 microns, and in particular having a mean particle size of not more than 15 microns. The micronized form of the compound (I) has the advantage of dissolving better and more rapidly due to its high surface area, and of penetrating well into the upper layers of the epidermis. Micronized forms of the compound (I) are novel and can be prepared by micronization techniques known in the art, e.g. by milling in appropriate mills and sieving through appropriate sieves.

The free base form of compound (I) wherein R represents ethyl occurs in two polymorphic forms; the higher melting polymorph I as a substantially crystallographically pure substance can be characterized by its peak maximum at about 127.6° C. with DSC; the lower melting polymorph II as a substantially crystallographically pure substance by its peak maximum at about 110.9° C. Polymorph I is more stable and slightly less soluble than polymorph II, and is the polymorphic form used preferably in the method according to the present invention. Polymorph I can conveniently be prepared by recrystallizing the free base form of compound (I) in a suitable solvent such as a ketone or an ester, e.g. acetone or ethyl acetate. Said recrystallization generally comprises dissolving the free base form of the compound of formula (I) in a hot solvent, concentrating the thus obtained solution, allowing the concentrate to cool and separating the precipitated crystals. Preferably, the solution is treated with active charcoal before concentrating. Further, it may be advantageous to seed the supersaturated solution from which polymorph I is to be crystallized with appropriate crystals of said polymorph I that have been obtained in previous runs. Polymorph I can be micronized as described hereinbefore, by milling in an appropriate mill and sieving the thus obtained product, for example, with an air-jet sifter using appropriate sieves such as 100 and 74 micrometer sieves. Polymorph II on the other hand can be obtained by recrystallizing the free base form of compound (I) in a suitable solvent such as 2-propanol, hexane, or methylbenzene. Selective crystallization of said polymorph II may be induced by seeding the supersaturated solution from which polymorph II is to be crystallized. Polymorph II also may be micronized although due care should be taken to avoid transition of polymorph II into polymorph I.

The compound (I) is most preferably applied to the affected areas of the body in the form of appropriate compositions, in particular cosmetic compositions. Said compositions contain the compound (I), preferably in a 0.05 to 1% concentration (weight by weight), in particular in a 0.1% to 0.5% concentration and preferably in a 0.1% to 0.2% concentration, and any known dermatologically acceptable carrier. Said compositions may take a wide variety of forms such as, for example, liquid forms, e.g. solutions, emulsions, gels or suspensions in aqueous, alcoholic or oily mediums, such as toilet waters, packs, lotions, skin milks or milky lotions and shampoos; or semi-liquid formulations, e.g. creams, hydrogels, gels, pastes, ointments, salves, tinctures and the like, or solid formulations, e.g. powders.

Said preparations contain, besides the compound (I), components usually employed in such preparations. Examples of such components are oils, fats, waxes, surfactants, humectants, penetration enhancing agents, thickening agents, lipid absorbents, anti-oxidants, viscosity stabilizers, chelating agents, buffers, preservatives, perfumes, fragrances, dyestuffs, lower alkanols, unsaturated alcohols and the like. If desired, further active ingredients may be incorporated in the compositions, e.g. antiinflammatory agents, antibacterials, antifungals, woundhealing agents, disinfectants, vitamins, sunscreens, antibiotics or anti-dandruff agents.

The compound (I) is advantageously used in cosmetical products useful for dealing with an impure skin or for preventing the development of skin impurities such as blemishes, comedones, pimples and the like. Examples of such cosmetic compositions are sun protecting products to be used before, during or after exposure to the sun, products for tanning without sun, skin-whitening products, anti-wrinkle products, daily used hygienic preparations for cleaning and caring such as soaps, shampoos, bath and shower products, shaving creams, foams or lotions, baby care products, hygienic tissues, products for intimate hygiene care, e.g. intimate cleansing products, and daily used cosmetic preparations such as creams, emulsions, gels, oils, lotions, skin milks, milk gels, tinted milk gels, face masks, deodorants, anti-perspirants, perfumes, toilet waters, eau de Cologne, depilatories, after-shaves, make-up articles, e.g. creams, tinted bases, powders, lipstick, cover sticks, eye-liners; products for removing make-up from the face and the eyes; hair care products, e.g. hair tints and bleaches, products for waving, straightening and fixing, setting products, cleansing products, conditioning products or hairdressing products; and the like cosmetical products. The liquid formulations may be packaged advantageously in any dispensing device adapted for topical administration, for example in flacons, bottles or also as a spray, either using an inert compressed gas as a propellant such as nitrogen or carbon dioxide, or alternatively using a pump to provide an aerosol. Solid formulations can be applied to the skin with powder puffs or directly with a cover stick. Alternatively, solid formulations such as granules, tablets or powders may also be dissolved in baths. Semi-liquid formulations can be packaged in suitable, art-known containers such as plastic, glass or ceramic pots, tubes, e.g. PVC-covered aluminum tubes.

Other particular compositions are those wherein the compound (I) is formulated in liposome-containing compositions. Different types of liposomes may be employed such as coarse (multilayer) liposomes or unilamellar liposomes and the like, which are formed, for example, with phosphatidyl cholines, ethanolamines, serines, sphingomyelins, cardiolipins, plasmalogens, phosphatidic acids, cerebrosides and the like. The viscosity of the liposomes can be increased by addition of one or more thickening agents such as xanthan gum, hydroxypropyl cellulose, hydroxypropyl methylcellulose and mixtures thereof. The aqueous component may consist of water optionally in admixture with electrolytes, buffers and other ingredients such as preservatives. Preferred electrolytes are calcium, sodium and potassium chloride. The organic component may consist of a solvent such as ethanol, glycerol, propylene glycol, a polyethylene glycol and a suitable phospholipid such as, lecithin, phosphatidyl choline, phosphatidyl ethanolamine, phosphatidyl serine, phosphatidyl inositol, lysophosphatidyl choline, phosphatidyl glycerol and the like. Other lipophilic additives which may be added to selectively modify the characteristics of the liposomes are, e.g. stearylamine, phosphatidic acid, tocopherol, cholesterol, lanolin and the like.

For preparing ointments, creams, toilet waters, skin milks, and the like, compound (I) is combined in intimate admixture with a cosmetically acceptable carrier. In ointments or creams, the carrier for example consists of 1 to 20%, in particular 5 to 15% of a humectant, 0.1 to 10%, in particular from 0.5 to 5% of a thickener, and water, or said carrier may consist of 70 to 99%, in particular 80 to 95% of a surfactant, and 0 to 20%, in particular 2.5 to 15% of a fat; or 80 to 99.9%, in particular 90 to 99% of a thickener; or 5 to 15% of a surfactant, 2–15% of a humectant, 0 to 80% of an oil, small (0 to $\leq 2\%$) amounts of preservative, colouring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (0 to <2%) of preservative, dyestuff and/or perfume. In a milk gel, the carrier typically consists of 50 to 80% of water, preferably 70 to 80% of water; 8 to 20%, preferably 10 to 15% of an alcohol; 1 to 10%, preferably 2 to 5% of a surfactant; 0.5 to 2% of one or more thickeners; and 0 to 3% of preservatives, humectants, nutritional factors, vitamins, astringents and/or perfumes. Other active ingredients may be incorporated at doses ranging from 0.005% to 0.5%, particularly from 0.01% to 0.1%.

Typical milk gel formulations comprise the active ingredient at the concentrations mentioned hereinabove; water; one or more gelling agents or thickeners such as, for example, cellulose derivatives, e.g. hydroxypropyl cellulose, hydroxypropyl methylcellulose, or carboxyvinylpolymers at a concentration of 0.02% to 4%, particularly 0.2% to 2% and preferably about 0.2% to 1.5%; one or more alcohols such as, for example, ethanol, propanol, butanol, pentanol, glycerol, propylene glycol, dodecatrienol in a concentration of 0.02% to 50%, particularly 0.5% to 30% and preferably about 0.5% to 20%. Said typical milk gel formulation may further comprise plant extracts, e.g. from aloe, arnica, birch, bladder wrack, gentian, ginseng, hamamelis (witch hazel), hawthorn, kina, lemon, nasturtium, rosemary and the like, at a concentration of from 0.1% to 35%, preferably from 0.5% to 12% and in particular from 1% to 3%; fatty ingredients such as paraffins at a concentration of from 0.1% to 30%, preferably from 0.2% to 10% and in particular from 1% to 5%; vitamins such as, for example, vitamin E (tocopherol) and derivatives, e.g. tocopheryl acetate, panthenol, and the like, at a concentration of 0.01% to 10%, preferably 0.1% to 8% and in particular 0.5% to 2%; antiinflammatory products of synthetic or natural origin, e.g. bisabolol, at a concentration of 0% to 5%, preferably 0.1% to 3% and in particular 0.2% to 0.5%; fragrances at a concentration of 0% to 2%, preferably 0.1% to 1% and in particular 0.3% to 0.5%; and optionally preservatives and/or antioxidants in an amount sufficient to prevent the degradation of the final composition.

Typical tinted formulations may be emulsions comprising the active ingredient at the concentrations mentioned hereinabove; water, one or more emulsifiers such as ethoxylated fatty alcohols, e.g. ceteth, laureth, myreth, oleth, steareth, trideth at a concentration of 0.1% to 10%, preferably 0.5% to 5%; one or more fatty components such as a $C_{8-22}$ fatty alcohol, preferably a $C_{12-18}$ fatty alcohol at a concentration of 0.1% to 10%, preferably 0.5% to 5%, or a mineral oil (petrolatum) at a concentration of 0.1% to 80%, preferably 1% to 30%; or a polyoxyethylated or -propylated fatty alcohol ether, e.g. polyoxypropylated stearyl ether, at a concentration of 1 to 40%, preferably 5 to 30%, and in particular 10 to 20%; one or more alcohols such as, for example, ethanol, propanol, butanol, pentanol, glycerol, propylene glycol, butylene glycol, dodecatrienol in a concentration of 0.1% to 25%, preferably 0.5% to 20%. Said tinted formulations obviously further comprise one or more pigments such as zinc oxide, kaolin, mica, iron oxide, titaniumdioxide and the like. Said tinted formulations may further also comprise plant extracts, e.g. from aloe, arnica, birch, bladder wrack, gentian, ginseng, hamamelis (witch hazel), hawthorn, kina, lemon, nasturtium, rosemary and the like, at a concentration of from 0.1% to 35%, preferably from 0.5% to 12% and in particular from 1% to 3%; a gelling agent such as a cellulose derivative or a carboxyvinyl polymer at a concentration of 0.1% to 1%; vitamins such as, for example, vitamin E (tocopherol) and derivatives, e.g. tocopheryl acetate, panthenol, and the like, at a concentration of 0.01% to 10%, preferably 0.1% to 8% and in particular 0.5% to 2%; antiinflammatory products of synthetic or natural origin, e.g. bisabolol, at a concentration of 0% to 5%, preferably 0.1% to 3% and in particular 0.2% to 0.5%; thickening agents, e.g. xanthan gum, at a concentration of 0.1% to 1%, preferably 0.2% to 0.5%; fragrances at a concentration of 0% to 2%, preferably 0. 1% to 1% and in particular 0.3% to 0.5%; and optionally preservatives and/or antioxidants in an amount sufficient to prevent the degradation of the final composition. Preferably the above formulations have a pH ranging from 5 to 7.5, particularly from 5.5 to 7. Said pH can be established by the addition of a base, e.g. sodium hydroxide, or an acid, e.g. lactic, citric or phosphoric acid, or a buffer, e.g. a citrate, phosphate, lactate or acetate buffer.

A typical coverstick formulation comprises the active ingredient at the concentrations mentioned hereinabove; one or more fatty substances such as a mineral oil (petrolatum) at a concentration of 1% to 70%, preferably 30% to 60%, or a paraffin at a concentration of 0. 1% to 30%, preferably 5% to 20%; triglycerides at a concentration of 0. 1% to 30%, preferably 1% to 10%; a fatty $C_{8-22}$ alcohol, preferably a $C_{12-18}$ fatty alcohol at a concentration of 0.1% to 40%, preferably 1% to 10%; a wax at a concentration of 0.1% to 10%; and optionally a sufficient amount of preservatives and/or antioxidants to prevent the degradation of the final composition; and optionally other ingredients such as fragrances, woundhealing products, pigments and the like.

In the aforementioned preparations, all % symbols refer to weight by weight percentage. The humectant, surfactant, oil, other active ingredient, etc. referred to in said preparations may be any such component used in the cosmetic arts. Further, when in the above compositions one or more of the components make up the major part of the composition, the other ingredients can evidently be not present at their indicated maximum concentration and therefore will make up the remainder of the composition.

EXPERIMENTAL PART

Example 1

Preparation of compound (I)

a) A stirred mixture of 50 grams of cis-1-acetyl-4-[4-[[2-(2, 4-dichlorophenyl)-2-(1H-imidazol-1-ylmethyl)-1,3- dioxolan-4-yl]methoxy]phenyl]piperazine, 105 grams of water and 35 grams of concentrated hydrochloric acid was heated at 80°–90° C. for 16 hours. The reaction mixture was cooled to room temperature (approximately 20°–25° C.) and 70 ml of dichloromethane and 30 ml of methanol were added. There was added dropwise 25 ml of sodium hydroxide solution (50% in water) while stirring and keeping the temperature of the reaction mixture below 30° C. by cooling with ice-water. After stirring for half an hour, there were added another 130 ml of dichloromethane and 170 ml of methanol. Stirring was continued for yet another half hour, the organic layer was separated and the organic solvent was distilled off under reduced pressure. The residue was taken up in 200 ml of dichloromethane.

b) To the residue there were added 52 grams of potassium carbonate and 12.25 grams of ethyl chloroformate were added dropwise while keeping the reaction temperature below 25° C. After stirring for two hours at room temperature, 112 grams of water were added and stirring was continued for four more hours. The organic layer was separated, dried, filtered and evaporated under reduced pressure. The residue was dissolved in 60 ml 4-methyl-2-pentanone by heating and crystallized by allowing the reaction mixture to cool spontaneously to room temperature. After cooling another four hours with ice-water, the precipitate was filtered off and dried in vacuo at 40° C., yielding 44.84 grams (84.9%) of (±)-ethyl cis-4-[4-[[2-(2,4-dichlorophenyl)-2-(1H-imidazol-1-ylmethyl)-1,3-dioxolan-4-yl]methoxy]phenyl]-1-piperazinecarboxylate.

c) A mixture of 6.5 grams of (±)-ethyl cis-4-[4-[[2-(2,4-dichlorophenyl)-2-(1H-imidazol-1-ylmethyl)-1,3-dioxolan-4-yl]methoxy]phenyl]-1-piperazinecarboxylate in 51.5 ml of acetone was heated to the reflux temperature and 3.23 grams of active coal (Norit A supra) were added. After refluxing another half hour, the reaction mixture was filtered over diatomaceous earth while hot. The filter was washed with hot acetone and the combined filtrates were concentrated to an end volume of about 25 ml. The reaction mixture was allowed to cool to 40° C. and was then seeded with polymorph I. The reaction mixture was allowed to cool further to room temperature and was then stirred for one hour while cooling with ice-water. The precipitate was filtered off and dried in vacuo at 40° C., yielding 5.35 parts (82.1%) of (±)-ethyl cis-4-[4-[[2-(2, 4-dichlorophenyl)-2-(1H-imidazol-1-ylmethyl)-1,3-dioxolan-4-yl]methoxy]phenyl]-1-piperazinecarboxylate (polymorph I); mp. 127.6° C.

COMPOSITION EXAMPLES

The following formulations exemplify typical compositions in accordance with the present invention.

"Active ingredient" (A.I.) as used throughout these examples relates to a compound of formula (I) or a cosmetically acceptable acid addition salt thereof.

Example 2

0.1% cream 75 mg stearyl alcohol, 2 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70° to 75° C. while using a homogenizer for liquids. The resulting emulsion is allowed to cool to below 25° C. while continuously mixing. A solution of 1 mg A.I., 1 mg polysorbate 80 and purified water and a solution of 2 mg sodium sulfite anhydrous in purified water are next added to the emulsion while continuously mixing. The cream is homogenized and filled into suitable tubes.

Example 3

0.2% liposome formulation

A mixture of 0.2 g A.I. microfine, 20 g phosphatidyl choline, 5 g cholesterol and 10 g ethyl alcohol is stirred and heated at 55°–60° C. until complete dissolution and is added to a solution of 0.2 g methyl paraben, 0.02 g propyl paraben, 0.15 g disodium edetate and 0.3 g sodium chloride in purified water while homogenizing. 0.15 g Hydroxypropyl-methylcellulose in purified water ad 100 g is added and the mixing is continued until swelling is complete.

Example 4

0.1% liposome formulation

A mixture of 10 g phosphatidyl choline and 1 g cholesterol in 7.5 g ethyl alcohol is stirred and heated at 40° C. until complete dissolution. 0.2 g A.I. microfine is dissolved in purified water by mixing while heating at 40° C. The alcoholic solution is added slowly to the aqueous solution while homogenizing during 10 minutes. 1.5 g Hydroxypropyl-methylcellulose in purified water is added while mixing until swelling is complete. The resulting solution is adjusted to pH 5.0 with sodium hydroxide 1N and diluted with the rest of the purified water ad 100 g.

I claim:

1. A cosmetic composition for reducing the greasiness of the skin, comprising a cosmetic vehicle and as active ingredient, from 0.05% to 1% by weight based on the total weight of the cosmetic composition of a compound of formula I

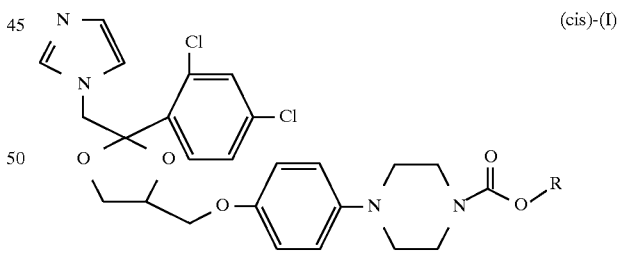

wherein R represents methyl or ethyl, or a cosmetically acceptable acid addition salt thereof, characterized in that said compound is micronized and has a particle size of less than 100 micron.

2. A cosmetic composition according to claim 1 comprising 0.1% to 0.2% of the active ingredient by weight based on the total weight of the cosmetic composition.

3. A cosmetic composition for reducing the greasiness of the skin, comprising a cosmetic vehicle and as active ingredient, from 0.05% to 1% by weight based on the total weight of the cosmetic composition of a compound of formula I

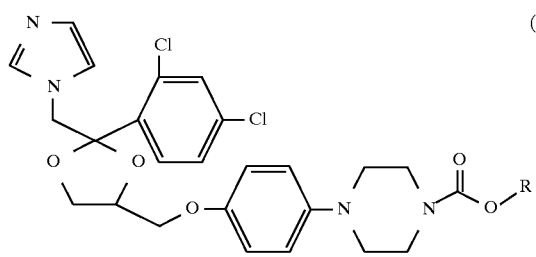

(cis)-(I)

wherein R represents ethyl, or a cosmetically acceptable acid addition salt thereof, characterized in that said compound is micronized and has a particle size of less than 100 micron and a peak maximum melting point, determined by DSC, of about 127.6° C.

4. A cosmetic composition according to claim 3 comprising 0.1% to 0.2% of the active ingredient by weight based on the total weight of the cosmetic composition.

* * * * *